United States Patent
Yuan et al.

(10) Patent No.: US 9,803,140 B2
(45) Date of Patent: Oct. 31, 2017

(54) LIQUID CRYSTAL COMPOUND AND LIQUID CRYSTAL COMPOSITION

(71) Applicant: SHIJIAZHUANG CHENGZHI YONGHUA DISPLAY MATERIALS CO., LTD., Hebei (CN)

(72) Inventors: Guoliang Yuan, Hebei (CN); Lei Zhao, Hebei (CN); Kui Wang, Hebei (CN); Mingxia Wang, Hebei (CN); Ruimao Hua, Hebei (CN); Jinsong Meng, Hebei (CN)

(73) Assignee: Shijiazhuang Chengzhi Yonghua Display Materials Co., Ltd., Shijiazhuang (CN)

( * ) Notice: Subject to any disclaimer, the term of this patent is extended or adjusted under 35 U.S.C. 154(b) by 0 days.

(21) Appl. No.: 15/161,010

(22) Filed: May 20, 2016

(65) Prior Publication Data
US 2017/0101581 A1     Apr. 13, 2017

(30) Foreign Application Priority Data

Oct. 13, 2015     (CN) .......................... 2015 1 0670395

(51) Int. Cl.
| | | |
|---|---|---|
| *G02F 1/1333* | (2006.01) | |
| *C09K 19/30* | (2006.01) | |
| *C07C 43/225* | (2006.01) | |
| *C09K 19/02* | (2006.01) | |
| *C09K 19/34* | (2006.01) | |
| *G02F 1/1362* | (2006.01) | |

(52) U.S. Cl.
CPC ........ *C09K 19/3066* (2013.01); *C07C 43/225* (2013.01); *C09K 19/0208* (2013.01); *C09K 19/3402* (2013.01); *G02F 1/1362* (2013.01); *C07C 2601/14* (2017.05); *C09K 2019/3422* (2013.01)

(58) Field of Classification Search
CPC ............ C09K 19/3066; C09K 19/0208; C09K 19/3402; C09K 2019/3422; G02F 1/1333; G02F 1/1362; C07C 43/225; C07C 2601/14

USPC .......................... 252/299.01, 299.61, 299.63
See application file for complete search history.

(56) References Cited

U.S. PATENT DOCUMENTS

| | | | | |
|---|---|---|---|---|
| 7,501,164 B2* | 3/2009 | Saito | ................. | C09K 19/3066 |
| | | | | 252/299.63 |
| 8,211,513 B2* | 7/2012 | Jansen | ............... | C09K 19/0275 |
| | | | | 252/299.61 |

* cited by examiner

*Primary Examiner* — Geraldina Visconti
(74) *Attorney, Agent, or Firm* — McCoy Russell LLP

(57) ABSTRACT

The present disclosure discloses a liquid crystal compound and a liquid crystal composition. The liquid crystal compound has a general structural formula as represented by formula I. The liquid crystal composition provided by the present disclosure has a lower rotary viscosity $\gamma_1$, can achieve a quick response, and further has an appropriate dielectric anisotropy $\Delta\varepsilon$, an appropriate optical anisotropy $\Delta n$, a high stability to heat and light, a high VHR numerical value especially in the case where the liquid crystal is under harsh conditions, and a stability to electric field and electromagnetic radiation. As a liquid crystal material for use in thin film transistor techniques (TFT-LCD), the material further has the properties of a wider nematic phase temperature range, an appropriate birefringence anisotropy, a very high electrical resistivity, a good anti-ultraviolet performance, a high charge holding rate, a low vapor pressure etc.

Formula I

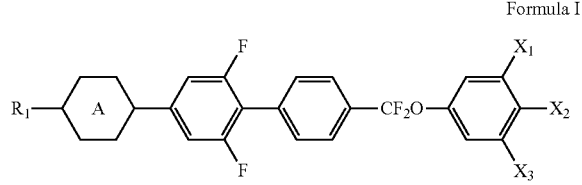

10 Claims, 3 Drawing Sheets

LIQUID CRYSTAL COMPOUND AND LIQUID CRYSTAL COMPOSITION

CROSS REFERENCE TO RELATED APPLICATION

This application claims priority to Chinese Patent Application No. 201510670395.0, entitled "Liquid Crystal Compound and Liquid Crystal Composition," filed Oct. 13, 2015, the entire contents of which are hereby incorporated by reference for all purposes.

TECHNICAL FIELD

The present disclosure belongs to the field of liquid crystals, and relates to a liquid crystal compound and a liquid crystal composition.

BACKGROUND ART

At present, the application range of liquid crystal compounds has expanded more and more widely, which can be used for various types of displays, electro-optical devices, sensors etc. The liquid crystal compounds for use in the above-mentioned display field are in a wide range of varieties, wherein the application in nematic phase liquid crystals is most extensive. Nematic phase liquid crystals have been used in passive twisted nematic (TN), super-twisted nematic (STN) matrix displays and systems having a thin filter transistor (TFT) active matrix.

With regard to the application field of thin film transistor techniques (TFT-LCD), although in recent years the market thereof has been very huge and the techniques also gradually become mature, the requirements on display techniques by people are also continuously increasing, especially in the aspects of achieving a quick response, reducing the driving voltage to reduce power consumption, etc. Liquid crystal materials, as one of important optoelectronic materials for liquid crystal displays, play an important role in improving the performance of liquid crystal displays.

As liquid crystal materials, they need to have good chemical and heat stabilities and stabilities to electric field and electromagnetic radiation. In addition, as a liquid crystal material for use in thin film transistor techniques (TFT-LCD), the material not only needs to have the stabilities as described above, but also should have the properties of a wider nematic phase temperature range, an appropriate birefringence anisotropy, a very high electrical resistivity, a good anti-ultraviolet performance, a high charge holding rate, a low vapor pressure etc.

With regard to the application in dynamic image display, such as a liquid crystal display television, in order to achieve a high quality display and eliminate the displayed image sticking and streaking, the liquid crystal is required to have a very fast response speed, and therefore the liquid crystal is required to have a lower rotary viscosity $\gamma_1$; in addition, in order to reduce the equipment energy consumption, the driving voltage of the liquid crystal is expected to be as low as possible, so improving the dielectric anisotropy $\Delta\varepsilon$ of the liquid crystal has an important significance for mixed liquid crystals.

SUMMARY OF THE PRESENT DISCLOSURE

An objective of the present disclosure is to provide a liquid crystal compound and a liquid crystal composition.

The liquid crystal compound provided by the present disclosure has a general structural formula as represented by formula I,

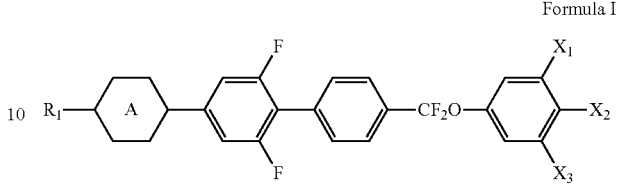

Formula I in said formula I, $R_1$ represents an alkyl having a carbon atom number of 1-9, a fluoro-substituted alkyl having a carbon atom number of 1-9, an alkoxy having a carbon atom number of 1-9, a fluoro-substituted alkoxy having a carbon atom number of 1-9, an alkenyl having a carbon atom number of 2-9, a fluoro-substituted alkenyl having a carbon atom number of 2-9, an alkenyloxy having a carbon atom number of 3-8 or an alkenyloxy having a carbon atom number of 3-8;

represents 1,4-phenylene, fluoro-substituted 1,4-phenylene, 1,4-cyclohexylidene, 1,4-cyclohexenylene or 1,4-cyclohexylidene with one or two —$CH_2$— being substituted by oxygen atoms;

$X_1$ and $X_3$ each independently represent hydrogen or fluorine; and $X_2$ represents hydrogen, fluorine, an alkyl having a carbon atom number of 1-9, an alkoxy having a carbon atom number of 1-9, a fluoro-substituted alkyl having a carbon atom number of 1-9, a fluoro-substituted alkoxy having a carbon atom number of 1-9 or an alkenyl having a carbon atom number of 2-9, and particularly can be —$OCF_3$.

In an example, in the definition of said $R_1$, said alkyl having a carbon atom number of 1-9 is a C1, C2, C3, C4, C5, C6, C7, C8 or C9 alkyl, or a C1-C5 alkyl, or a C1-C4 alkyl, or a C1-C3 alkyl, or a C1-C2 alkyl, or a C2-C5 alkyl, or a C2-C4 alkyl, or a C2-C3 alkyl, or a C3-C5 alkyl, or a C3-C4 alkyl or a C4-C5 alkyl;

said fluoro-substituted alkyl having a carbon atom number of 1-9 is a C1, C2, C3, C4, C5, C6, C7, C8 or C9 fluoro-substituted alkyl, or a C1-C5 fluoro-substituted alkyl, or a C1-C4 fluoro-substituted alkyl, or a C1-C3 fluoro-substituted alkyl, or a C1-C2 fluoro-substituted alkyl, or a C2-C5 fluoro-substituted alkyl, or a C2-C4 fluoro-substituted alkyl, or a C2-C3 fluoro-substituted alkyl, or a C3-C5 fluoro-substituted alkyl, or a C3-C4 fluoro-substituted alkyl, or a C4-C5 fluoro-substituted alkyl;

said alkoxy having a carbon atom number of 1-9 is a C1, C2, C3, C4, C5, C6, C7, C8 or C9 alkoxy, or a C1-C5 alkoxy, or a C1-C4 alkoxy, or a C1-C3 alkoxy, or a C1-C2 alkoxy, or a C2-C5 alkoxy, or a C2-C4 alkoxy, or a C2-C3 alkoxy, or a C3-C5 alkoxy, or a C3-C4 alkoxy or a C4-C5 alkoxy;

said fluoro-substituted alkoxy having a carbon atom number of 1-9 is a C1, C2, C3, C4, C5, C6, C7, C8 or C9 fluoro-substituted alkoxy, or a C1-C5 fluoro-substituted alkoxy, or a C1-C4 fluoro-substituted alkoxy, or a C1-C3 fluoro-substituted alkoxy, or a C1-C2 fluoro-substituted alkoxy, or a C2-C5 fluoro-substituted alkoxy, or a C2-C4 fluoro-substituted alkoxy, or a C2-C3 fluoro-substituted alkoxy, or a C3-C5 fluoro-substituted alkoxy, or a C3-C4 fluoro-substituted alkoxy, or a C4-C5 fluoro-substituted alkoxy;

said alkenyl having a carbon atom number of 2-9 is a C2, C3, C4, C5, C6, C7, C8 or C9 alkenyl, or a C2-C5 alkenyl, a C2-C4 alkenyl, or a C2-C3 alkenyl, or a C3-C5 alkenyl, or a C3-C4 alkenyl or a C4-C5 alkenyl;

said alkenyl substituted by a fluorine atom and having a carbon atom number of 2-9 is a C2, C3, C4, C5, C6, C7, C8 or C9 alkenyl substituted by a fluorine atom, or a C2-C5 alkenyl substituted by a fluorine atom, or a C2-C4 alkenyl substituted by a fluorine atom, or a C2-C3 alkenyl substituted by a fluorine atom, or a C3-C5 alkenyl substituted by a fluorine atom, or a C3-C4 alkenyl substituted by a fluorine atom or a C4-C5 alkenyl substituted by a fluorine atom;

said alkenyloxy having a carbon atom number of 3-8 is a C3, C4, C5, C6, C7 or C8 alkenyloxy, or a C3-C5 alkenyloxy, or a C3-C4 alkenyloxy or a C4-C5 alkenyloxy; and said alkenyloxy substituted by a fluorine atom and having a carbon atom number of 3-8 is a C3, C4, C5, C6, C7 or C8 alkenyloxy substituted by a fluorine atom, or a C3-C5 alkenyloxy substituted by a fluorine atom, or a C3-C4 alkenyloxy substituted by a fluorine atom or a C4-C5 alkenyloxy substituted by a fluorine atom.

In an example, said compound as represented by formula I is a compound of formula IA, Formula IA

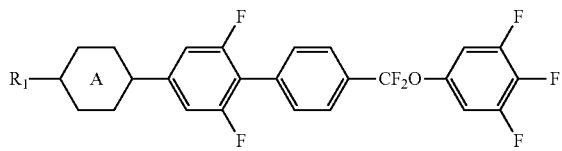

in said formula IA, both the definitions of $R_1$ and

are identical to the definition of $R_1$ in the above-mentioned formula I.

In an example, said compound as represented by formula I is any one of the compounds as represented by formulae I1 to I12:

I1

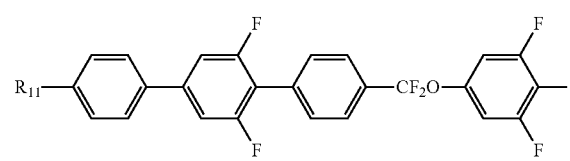

I2

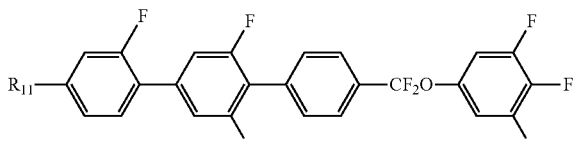

I3

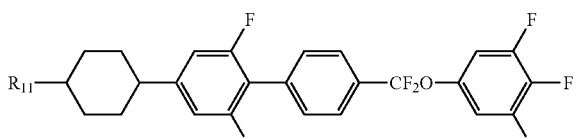

I4

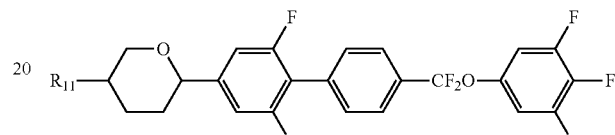

I5

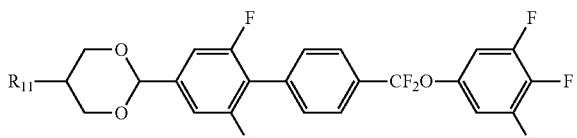

I6

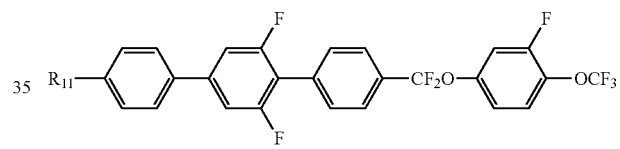

I7

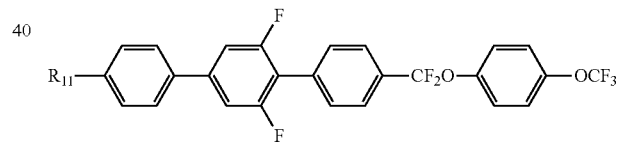

I8

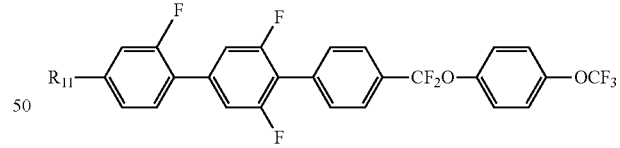

I9

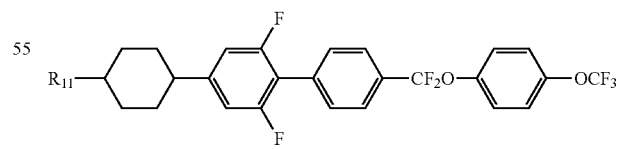

I10

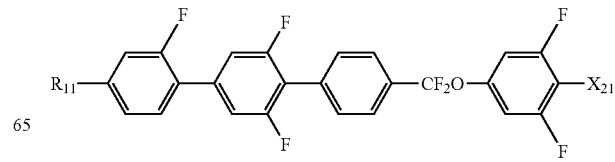

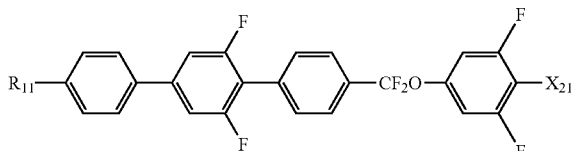

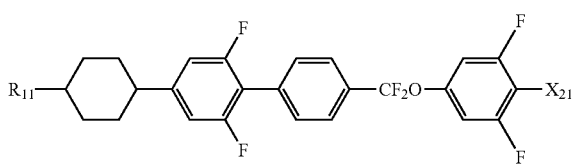

in said formulae I1 to I12, $R_{11}$ represents an alkyl having a carbon atom number of 1-5; and $X_{21}$ represents an alkyl having a carbon atom number of 1-5, an alkoxy having a carbon atom number of 1-5, an alkenyl having a carbon atom number of 2-5, a fluoro-substituted alkyl having a carbon atom number of 1-5 or a fluoro-substituted alkoxy having a carbon atom number of 1-5.

According to different $R_1$,

$X_1$, $X_2$ and $X_3$, the compounds as represented by formula I are thus slightly different in performance. They can be used as base materials for a liquid crystal mixture, and can also be added, as additive materials, into the liquid crystal base materials composed of other types of compounds, for example, to improve the dielectric anisotropy $\Delta\in$ and/or rotary viscosity $\gamma_1$ and/or threshold voltage $V_{th}$ and/or contrast at a low temperature and/or optical anisotropy $\Delta n$ and/or clearing point Cp of the liquid crystal mixture.

The compounds as represented by formula I have a very large dielectric anisotropy $\Delta\in$ which is between 10-30, and are strong polarity monomers, especially when $X_1$, $X_2$ and $X_3$ are each substituted by a fluorine atom, the $\Delta\in$ of, for example, the compound as represented by formula I2 can reach 30; therefore, it is very advantageous to improve the $\Delta\in$ of the liquid crystal mixture and reduce the driving voltage of the liquid crystal.

The optical anisotropy $\Delta n$ of the compounds as represented by formula I have a slightly wider range which is generally more appropriate as the structure of

changes, wherein when

is a benzene ring, $\Delta n$ is larger and is not less than 0.200; and when

is cyclohexane, $\Delta n$ is smaller and is about 0.15.

In addition, the compounds as represented by formula I have a low rotary viscosity $\gamma_1$ and a large elastic constant, which are advantageous to improve the response speed of the liquid crystal mixture; and have better ultraviolet light and heat stabilities, and are especially suitable for developing a liquid crystal formulation having higher image sticking requirements.

In addition, a liquid crystal mixture containing component A also falls within the scope of protection of the present disclosure, wherein said component A is composed of at least one of the above-mentioned compounds as represented by formula I provided by the present disclosure; and said liquid crystal mixture can further comprise components B and C;

said component B is composed of at least one of the compounds as represented by formula II; and said component C is composed of at least one of the compounds as represented by formula III;

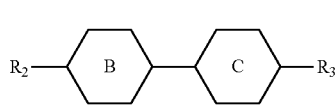

Formula II

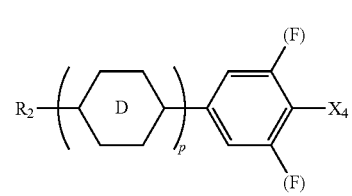

Formula III in said formulae II and III, $R_2$, $R_3$ and $R_4$ are each selected from a C1-C6 alkyl, or a C2-C6 alkenyl or a C1-C6 alkoxy;

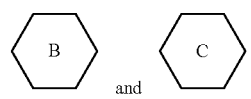

each independently represent 1,4-cyclohexylidene, 1,4-cyclohexenylene or 1,4-phenylene;

is selected from at least one of 1,4-cyclohexylidene, 1,4-cyclohexenylene, 1,4-phenylene and fluoro-substituted 1,4-phenylene;

p is 2 or 3;

(F) represents H or F; and $X_4$ is F, Cl or $-OCF_3$.

Of course, said liquid crystal mixture also can be composed of only said components A, B and C.

In one example, said compound as represented by formula II is any one of the compounds as represented by formulae II1 to II13:
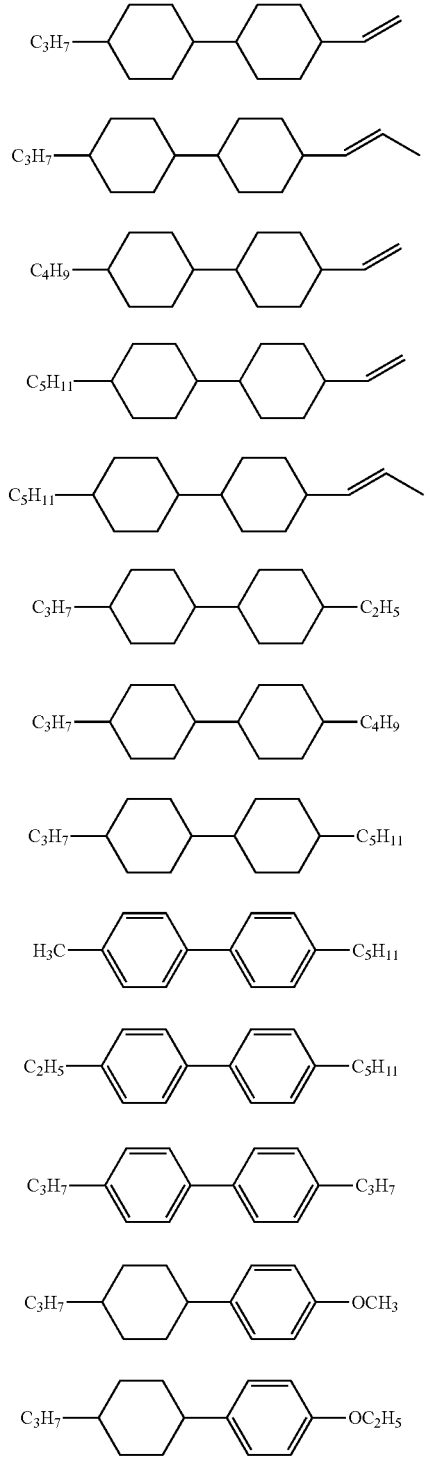
said compound as represented by formula III is any one of the compounds as represented by formulae III1 to III22:
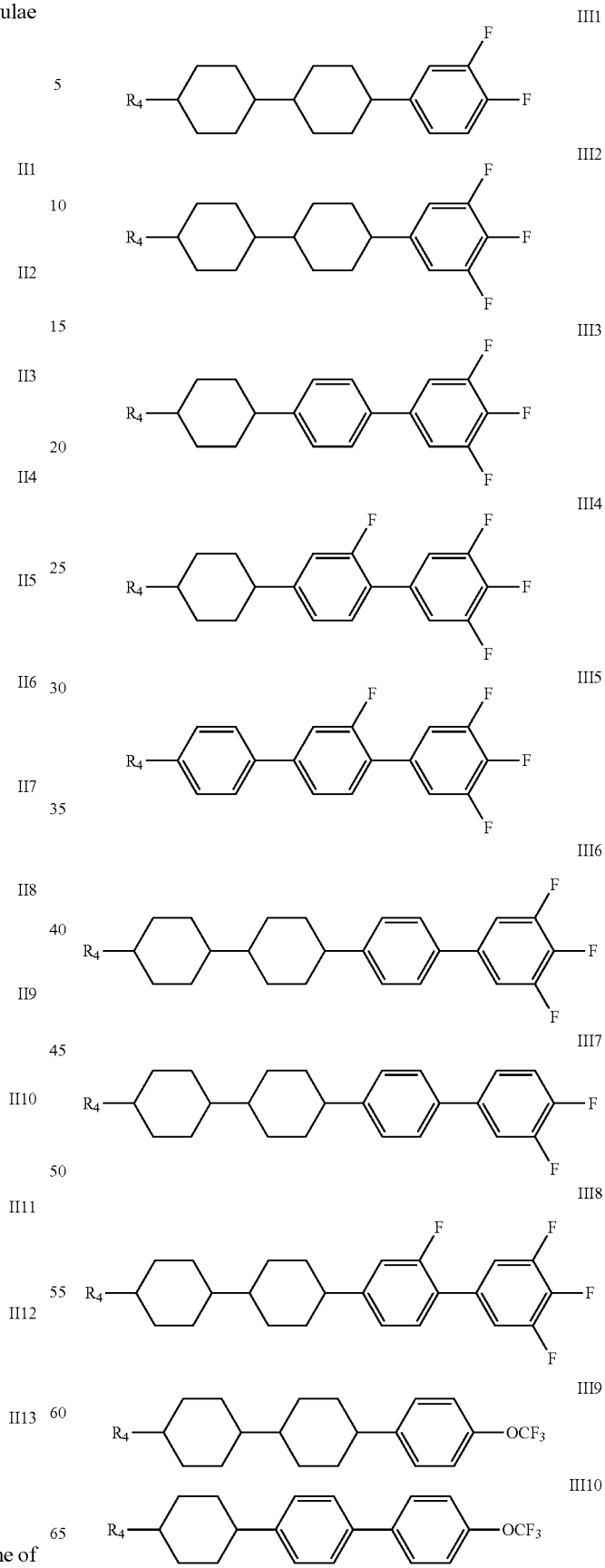

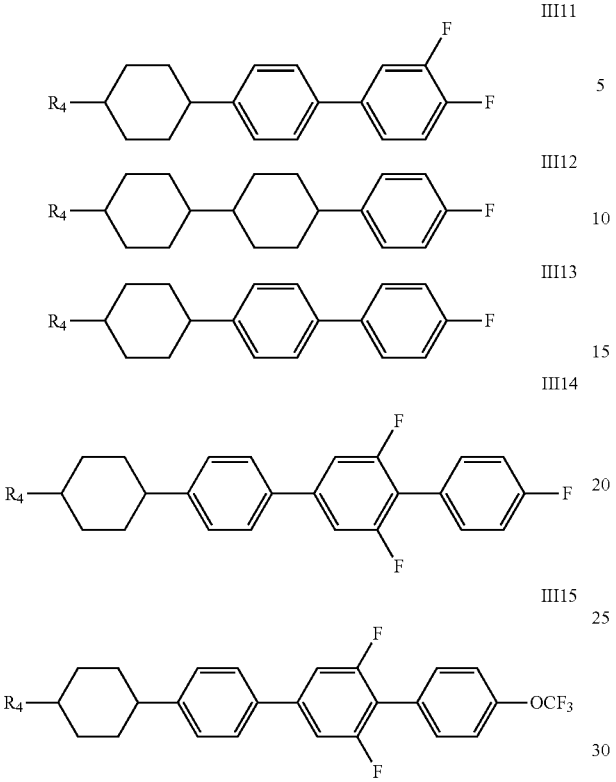
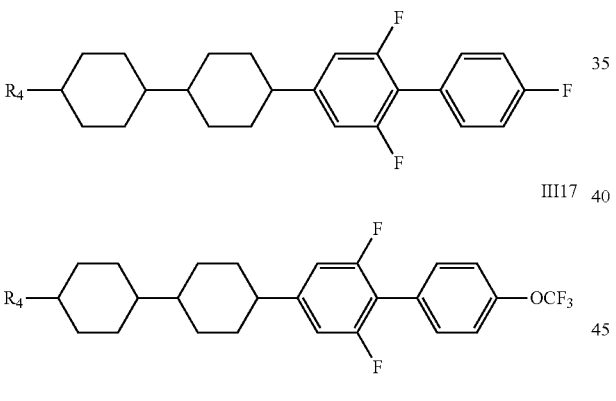
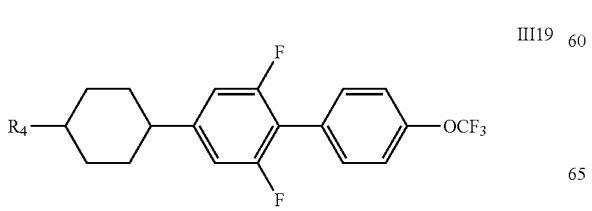

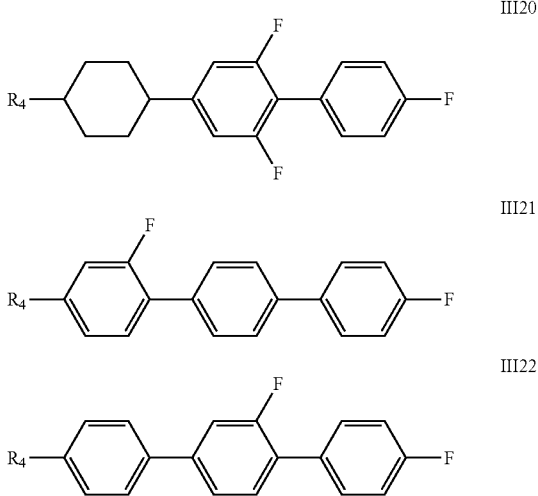

in said formulae III1 to III22, $R_4$ is selected from at least one of a C1-C6 alkyl, a C2-C6 alkenyl and a C1-C6 alkoxy.

Said liquid crystal mixture further comprises at least one of components D, E and F;

said component D is composed of at least one of the compounds as represented by formula IV;

Formula IV

in said formula IV, $R_{51}$ and $R_{52}$ are each selected from any one of a C1-C6 alkyl, a C2-C6 alkenyl and a C1-C6 alkoxy; m is 1 or 2; and

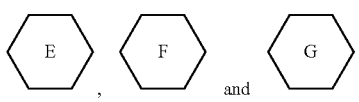

are each selected from at least one of 1,4-cyclohexylidene, 1,4-cyclohexenylene, 1,4-phenylene and fluoro-substituted 1,4-phenylene;

said component E is composed of at least one of the compounds as represented by formula V;

Formula V

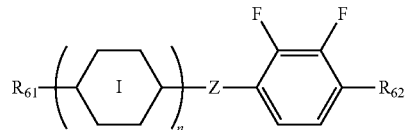

in said formula V, $R_{61}$ and $R_{62}$ are each selected from any one of a C1-C6 alkyl, a C2-C6 alkenyl and a C1-C6 alkoxy;

n is 1 or 2;

is selected from at least one of 1,4-cyclohexylidene, 1,4-cyclohexenylene, 1,4-phenylene and fluoro-substituted 1,4-phenylene;

Z is a single bond, —CH₂O—, —COO— or —CH₂CH₂—; and said component F is composed of at least one of the compounds as represented by formula VI;

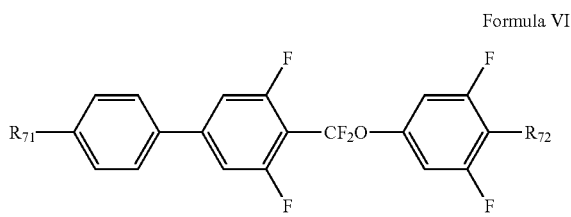

Formula VI in said formula VI, $R_{71}$ and $R_{72}$ are each selected from any one of a C1-C6 alkyl, a C2-C6 alkenyl and a C1-C6 alkoxy.

In one example, in the definitions of the substituent groups in said formulae II to VI, said C1-C6 alkyl is selected from at least one of a C1, C2, C3, C4, C5 or C6 alkyl, or a C2-C6 alkyl, or a C3-C6 alkyl, a C4-C6 alkyl, a C5-C6 alkyl, a C1-C5 alkyl, C2-C5 alkyl, a C3-C5 alkyl, a C4-C5 alkyl, C1-C4 alkyl, a C2-C4 alkyl, a C3-C4 alkyl, C1-C3 alkyl, a C1-C2 alkyl and a C2-C3 alkyl;

said C1-C6 alkoxy is selected from at least one of a C1, C2, C3, C4, C5 or C6 alkoxy, or a C2-C6 alkoxy, a C3-C6 alkoxy, a C4-C6 alkoxy, a C5-C6 alkoxy, a C1-C5 alkoxy, a C2-C5 alkoxy, a C3-C5 alkoxy, a C4-C5 alkoxy, a C1-C4 alkoxy, a C2-C4 alkoxy, a C3-C4 alkoxy, a C1-C3 alkoxy, a C1-C2 alkoxy and a C2-C3 alkoxy;

said C2-C6 alkenyl is selected from at least one of a C2, C3, C4, C5 or C6 alkenyl, or a C2-C6 alkenyl, a C3-C6 alkenyl, a C4-C6 alkenyl, a C5-C6 alkenyl, a C2-C5 alkenyl, a C3-C5 alkenyl, a C4-C5 alkenyl, a C2-C4 alkenyl, a C3-C4 alkenyl and a C2-C3 alkenyl;

the mass parts of the components in said liquid crystal mixture may be as follows, respectively:

component A: 5-25 parts, and in one example may be 6, 12, 15, 18, 20, 23 or 25 parts;

component B: 15-45 parts, and in one example may be 18, 25, 30, 33, 35, 40 or 42 parts;

component C: 5-45 parts, and in one example may be 8, 20, 25, 28, 35 or 40 parts;

component D: 5-25 parts, and in one example may be 6, 8, 11, 15 or 23 parts;

component E: 5-25 parts, and in one example may be 7 or 11 parts; and component F: 5-25 parts, and in one example may be 8, 12, 14, 18 or 19 parts.

Said liquid crystal mixture may be any one of the following liquid crystal mixtures a to g:

said liquid crystal mixture a comprises, or consists of, the following components in parts by mass:

| | |
|---|---|
| 3CCB(3F,4F) | 8-12 |
| 4CCBOCF3 | 8-12 |
| VCCB(3F,4F) | 10-15 |
| 2CCBB(3F,4F) | 5-10 |
| 3CCV | 15-20 |
| 3BB(3F,5F)BCF2OB(3F,4F,5F) | 5-10 |
| 3CCB1 | 10-15 |
| 3BB(3F,5F)CF2OB(3F,5F)O2 | 10-15 |
| 3BB(3F,5F)CF2OB(3F,5F)4 | 10-15; | said liquid crystal mixture a may comprise, or consist of, the following components in parts by mass:

| | |
|---|---|
| 3CCB(3F,4F) | 10 |
| 4CCBOCF3 | 10 |
| VCCB(3F,4F) | 12 |
| 2CCBB(3F,4F) | 8 |
| 3CCV | 18 |
| 3BB(3F,5F)BCF2OB(3F,4F,5F) | 6 |
| 3CCB1 | 11 |
| 3BB(3F,5F)CF2OB(3F,5F)O2 | 12 |
| 3BB(3F,5F)CF2OB(3F,5F)4 | 13; | said liquid crystal mixture b comprises, or consists of, the following components in parts by mass:

| | |
|---|---|
| 4CCB(3F,4F) | 5-10 |
| 2CCBOCF3 | 5-10 |
| VCCB(3F,4F) | 10-15 |
| 3CCV | 18-22 |
| 3CBO1 | 3-8 |
| 3BB(3F,5F)BCF2OB(3F,4F,5F) | 3-8 |
| 3CB(3F,5F)BCF2OB(3F,4F,5F) | 5-10 |
| 3CCB1 | 5-10 |
| VCCB1 | 10-15 |
| VCBB2 | 5-10 |
| 5BB(3F,5F)CF2OB(3F,5F)4 | 10-15; | said liquid crystal mixture b may comprise, or consist of, the following components in parts by mass:

| | |
|---|---|
| 4CCB(3F,4F) | 9 |
| 2CCBOCF3 | 8 |
| VCCB(3F,4F) | 11 |
| 3CCV | 20 |
| 3CBO1 | 5 |
| 3BB(3F,5F)BCF2OB(3F,4F,5F) | 5 |
| 3CB(3F,5F)BCF2OB(3F,4F,5F) | 7 |
| 3CCB1 | 6 |
| VCCB1 | 11 |
| VCBB2 | 6 |
| 5BB(3F,5F)CF2OB(3F,5F)4 | 12; | said liquid crystal mixture c comprises, or consists of, the following components in parts by mass:

| | |
|---|---|
| 4CCB(3F,4F) | 5-10 |
| 2CCBOCF3 | 5-10 |
| 3BBB(2F,4F) | 5-10 |
| 3CCV | 28-32 |
| 3CCV1 | 1-5 |
| 3BB(3F,5F)BCF2OB(3F,4F,5F) | 5-10 |
| 3CB(3F,5F)BCF2OB(3F)OCF3 | 5-10 |
| 3CCB1 | 5-10 |
| V2CCB1 | 5-10 |
| 5BB(3F,5F)CF2OB(3F,5F)4 | 10-15; | said liquid crystal mixture c may comprise, or consist of, the following components in parts by mass:

| | |
|---|---|
| 4CCB(3F,4F) | 7 |
| 2CCBOCF3 | 7 |
| 3B(3F)BB(4F) | 6 |
| 3CCV | 30 |
| 3CCV1 | 3 |
| 3BB(3F,5F)BCF2OB(3F,4F,5F) | 9 |
| 3CB(3F,5F)BCF2OB(3F)OCF3 | 9 |
| 3CCB1 | 6 |
| V2CCB1 | 9 |
| 5BB(3F,5F)CF2OB(3F,5F)4 | 14; | said liquid crystal mixture d comprises, or consists of, the following components in parts by mass:

| | |
|---|---|
| 2CCB(3F,4F) | 5-10 |
| 3CCV | 33-37 |
| 3CBO1 | 1-5 |
| 1BB5 | 3-8 |
| 3BB(3F,5F)BCF2OB(3F,4F,5F) | 5-10 |
| 4CB(3F,5F)BCF2OB(3F,4F,5F) | 5-10 |
| 3B(3F)B(3F,5F)BCF2OB(3F,5F)O2 | 5-10 |
| 3CBB1 | 5-10 |
| 5BB(3F,5F)CF2OB(3F,5F)4 | 8-12 |
| 5BB(3F,5F)CF2OB(3F,5F)2V | 5-10; | said liquid crystal mixture d may comprise, or consist of, the following components in parts by mass:

| | |
|---|---|
| 2CCB(3F,4F) | 8 |
| 3CCV | 35 |
| 3CBO1 | 2 |
| 1BB5 | 5 |
| 3BB(3F,5F)BCF2OB(3F,4F,5F) | 8 |
| 4CB(3F,5F)BCF2OB(3F,4F,5F) | 7 |
| 3B(3F)B(3F,5F)BCF2OB(3F,5F)O2 | 8 |
| 3CBB1 | 8 |
| 5BB(3F,5F)CF2OB(3F,5F)4 | 10 |
| 5BB(3F,5F)CF2OB(3F,5F)2V | 9; | said liquid crystal mixture e comprises, or consists of, the following components in parts by mass:

| | |
|---|---|
| 2CCB(3F,4F) | 5-10 |
| 3CCBB(3F,4F) | 3-8 |
| VCCBOCF3 | 10-15 |
| 1BB5 | 3-8 |
| 3CCV | 22-28 |
| 3BB(3F,5F)BCF2OB(3F,4F,5F) | 5-10 |
| 4CB(3F,5F)BCF2OB(3F,4F,5F) | 5-10 |
| 3B(3F)B(3F,5F)BCF2OB(3F,5F)O2 | 3-8 |
| 3CBB1 | 5-10 |
| 3BB(2F,3F)O2 | 10-15 |
| 5BB(3F,5F)CF2OB(3F,5F)2V | 5-10; | said liquid crystal mixture e may comprise, or consist of, the following components in parts by mass:

| | |
|---|---|
| 2CCB(3F,4F) | 8 |
| 3CCBB(3F,4F) | 5 |
| VCCBOCF3 | 12 |
| 1BB5 | 5 |
| 3CCV | 25 |
| 3BB(3F,5F)BCF2OB(3F,4F,5F) | 8 |
| 4CB(3F,5F)BCF2OB(3F,4F,5F) | 7 |
| 3B(3F)B(3F,5F)BCF2OB(3F,5F)O2 | 5 |
| 3CBB1 | 6 |
| 3BB(2F,3F)O2 | 11 |
| 5BB(3F,5F)CF2OB(3F,5F)2V | 8; | said liquid crystal mixture f comprises, or consists of, the following components in parts by mass:

| | |
|---|---|
| 2CCB(3F,4F) | 5-10 |
| 3CCBB(3F,4F) | 3-8 |
| VCCBOCF3 | 10-15 |
| 4CCV | 3-8 |
| 3CCV | 30 |
| 3BB(3F,5F)BCF2OB(3F,4F,5F) | 10 |
| 4CB(3F,5F)BCF2OB(3F,4F,5F) | 3-8 |
| 3CB(2F,3F)O2 | 5-10 |
| 5BB(3F,5F)CF2OB(3F,5F)2V | 5-10 |
| 3BB(3F,5F)CF2OB(3F,5F)4 | 8-12; | said liquid crystal mixture f may comprise, or consist of, the following components in parts by mass:

| | |
|---|---|
| 2CCB(3F,4F) | 8 |
| 3CCBB(3F,4F) | 5 |
| VCCBOCF3 | 12 |
| 4CCV | 5 |
| 3CCV | 30 |
| 3BB(3F,5F)BCF2OB(3F,4F,5F) | 10 |
| 4CB(3F,5F)BCF2OB(3F,4F,5F) | 5 |
| 3CB(2F,3F)O2 | 7 |
| 5BB(3F,5F)CF2OB(3F,5F)2V | 8 |
| 3BB(3F,5F)CF2OB(3F,5F)4 | 10; | said liquid crystal mixture g comprises, or consists of, the following components in parts by mass:

| | |
|---|---|
| 2CCB(3F,4F) | 5-10 |
| 3CCB(3F,4F) | 3-8 |
| VCCBOCF3 | 8-12 |
| 3CCBOCF3 | 10-15 |
| 4CCV | 3-8 |
| 3CCV | 28-32 |
| 3CBO2 | 3-8 |
| 3H[3O,5O]B(3F,5F)BCF2OB(3F,4F,5F) | 5-10 |
| 3B(3F)B(3F,5F)BCF2OB(3F,4F,5F) | 8-12 |
| 4CB(3F,5F)BCF2OB(3F,4F,5F) | 5-10; | and
said liquid crystal mixture g may comprise, or consist of, the following components in parts by mass:

| | |
|---|---|
| 2CCB(3F,4F) | 8 |
| 3CCB(3F,4F) | 5 |
| VCCBOCF3 | 10 |
| 3CCBOCF3 | 12 |
| 4CCV | 5 |
| 3CCV | 30 |
| 3CBO2 | 5 |
| 3H[3O,5O]B(3F,5F)BCF2OB(3F,4F,5F) | 9 |
| 3B(3F)B(3F,5F)BCF2OB(3F,4F,5F) | 10 |
| 4CB(3F,5F)BCF2OB(3F,4F,5F) | 6. |

In the above-mentioned liquid crystal monomer structures represented by codes, the code representation methods for the liquid crystal ring structures, terminal groups and linking groups are shown in tables 1 and 2.

In addition, a liquid crystal display element or liquid crystal display containing the above-mentioned compound as represented by formula I or liquid crystal mixture provided by the present disclosure and the use of the compound as represented by formula I or liquid crystal mixture in the preparation of a liquid crystal display element or liquid crystal display also fall within the scope of protection of the present disclosure.

Said liquid crystal display element or liquid crystal display may be an active-matrix addressing liquid crystal display element or an active-matrix addressing liquid crystal display;

said active matrix display element may be a TN-TFT, an in-plane switching thin film transistor (IPS-TFT) or fringe-field switching thin film transistor (FFS-TFT) liquid crystal display element; and said active-matrix addressing liquid crystal display may be a TN-TFT, IPS-TFT or FFS-TFT liquid crystal display;

said IPS-TFT liquid crystal display element may be an in-plane switching liquid crystal display element;

said FFS-TFT liquid crystal display element may be a fringe field switching liquid crystal display element;

said IPS-TFT liquid crystal display may be an in-plane switching liquid crystal display; and said FFS-TFT liquid crystal display may be a fringe field switching liquid crystal display.

The liquid crystal composition provided by the present disclosure has a lower rotary viscosity $\gamma_1$, can achieve a quick response, and further has an appropriate dielectric anisotropy $\Delta\epsilon$, an appropriate optical anisotropy $\Delta n$, a high stability to heat and light, a high voltage holding rate (VHR) numerical value especially in the case where the liquid crystal is under harsh conditions, and a stability to electric field and electromagnetic radiation. As a liquid crystal material for use in thin film transistor techniques (TFT-LCD), the material further has the properties of a wider nematic phase temperature range, an appropriate birefringence anisotropy, a very high electrical resistivity, a good anti-ultraviolet performance, a high charge holding rate, a low vapor pressure etc.

PARTICULAR EMBODIMENTS

The present disclosure is further described as below in combination with particular embodiments, but the present disclosure is not limited to the following embodiments. Said methods, if not otherwise indicated, are all conventional methods. Said raw materials, if not otherwise indicated, can all be available through public commercial approaches.

Figure 1:
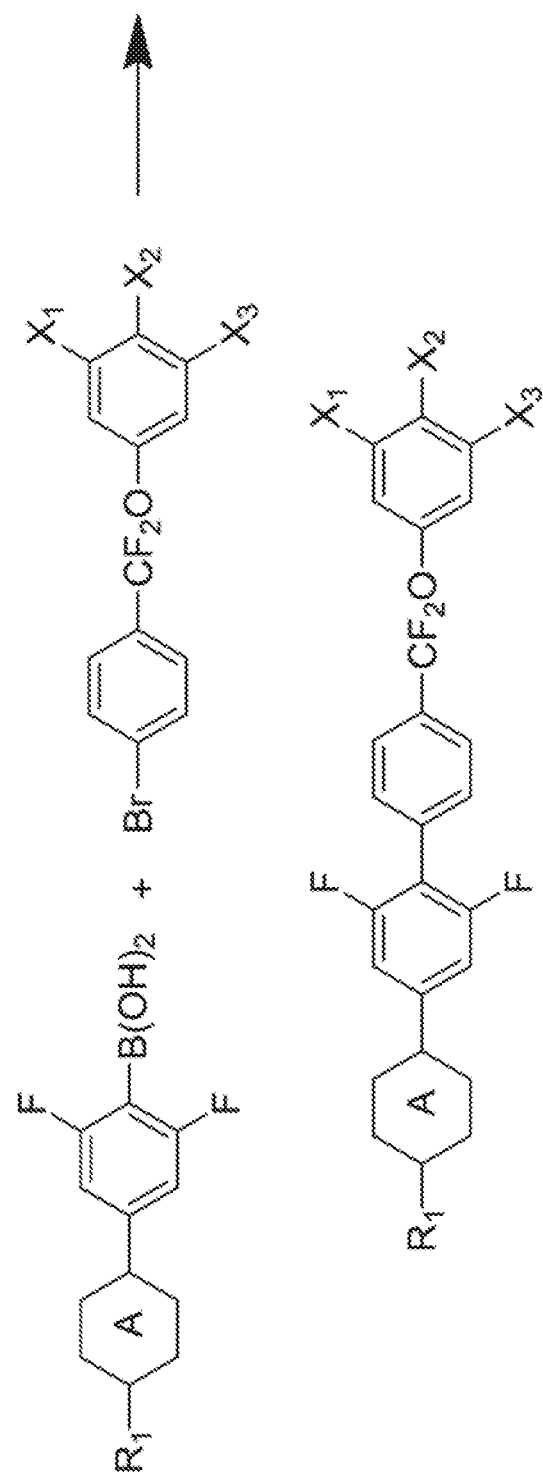
FIG. 1 shows a preparation flowchart of a compound as represented by formula I.
Figure 2:
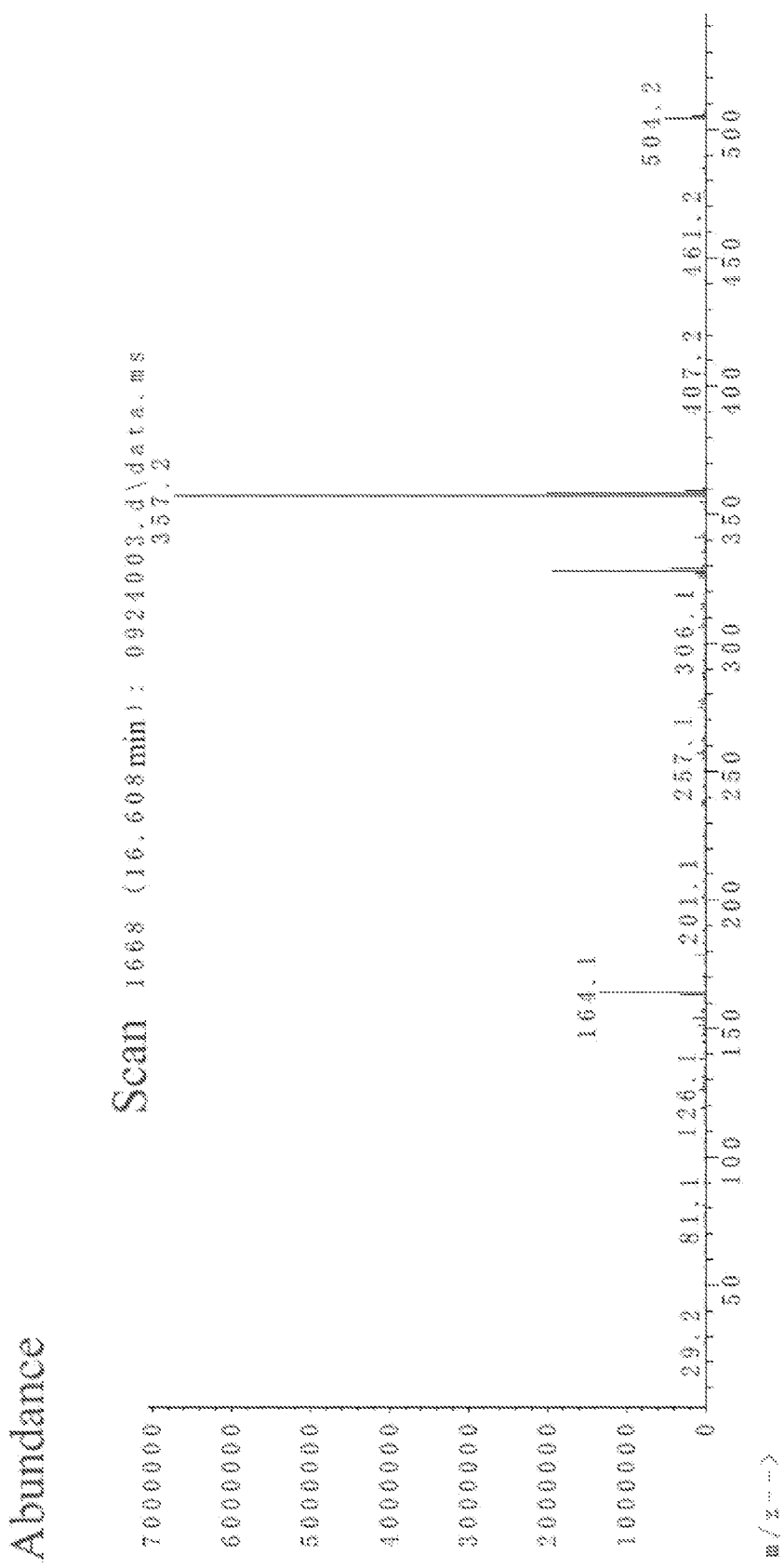
FIG. 2 shows the mass spectrum of a product obtained in embodiment 1.

The compound as represented by formula I can be prepared according to the method as shown in FIG. 1. The synthetic method has an advantage of simple and convenient synthesis, and is very low in synthesis cost and free of pollution during the synthesis. The compound of formula I can be obtained through synthesis by one-step SUZUKI coupling, wherein tetrakis(triphenylphosphine)palladium, Pd/C, Pd-132 etc. can be used as a catalyst, and the synthesis process can be achieved under alkaline conditions in an aqueous or anhydrous environment. Sodium carbonate, sodium bicarbonate, potassium carbonate, potassium phosphate etc. can be used as an alkali; toluene, ethanol, N,N-dimethylformamide, water, tetrahydrofuran etc. can be used as a solvent; the reaction is generally completed under a reflux condition for 1-6 hours, and the reaction progress can be tracked by thin layer chromatography (TLC).

The reaction process is generally monitored through TLC, and the post-treatments after the reaction is completed are generally water washing, extracting, combining organic phases and then drying, evaporating and removing the solvent under a reduced pressure, recrystallization and column chromatographic separation; and a person skilled in the art would be able to achieve the present disclosure according to the following description.

Figure 3:
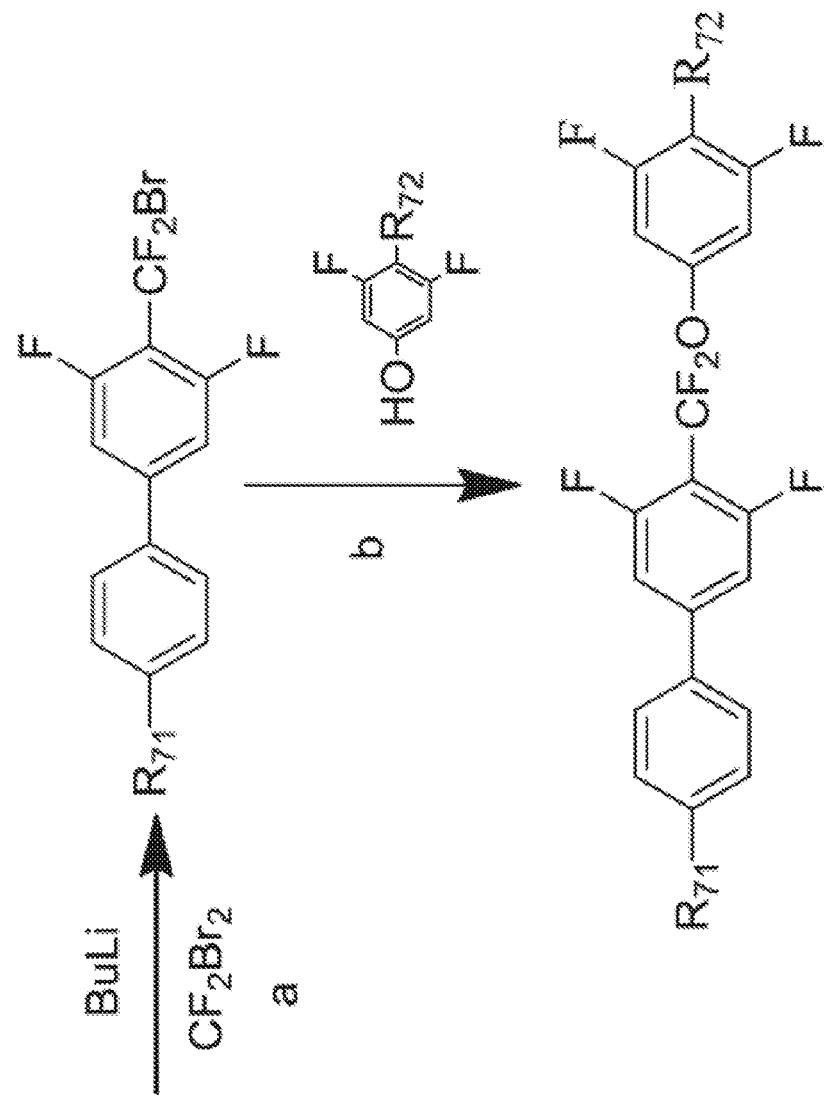
FIG. 3 shows a preparation flowchart of a compound as represented by formula VI.

The compound as represented by formula VI, as one of the components of the liquid crystal mixture, can be prepared according to the method as shown in FIG. 3, wherein the reaction condition a is BuLi, $CF_2Br_2$, THF and $-70°$ C.; and the reaction condition b is DMF, $K_2CO_3$ and $100°$ C.

The principle, operation process, conventional post-treatments, and the means of passing through a silica gel column, recrystallization and purification, etc. of such a method are well known to a person skilled in the art of synthesis, and according to the following introduction, the synthesis process can be fully achieved to obtain the target product.

The reaction process is generally monitored through TLC, and the post-treatments after the reaction is completed are generally water washing, extracting, combining organic phases and then drying, evaporating and removing the solvent under a reduced pressure, recrystallization and column chromatographic separation; and a person skilled in the art would be able to achieve same according to the description presented herein.

For example, a component with a code 3BB(3F,5F)CF2OB(3F,5F)O2 can be prepared according to the following method:

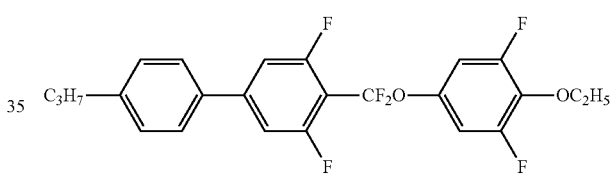

step 1

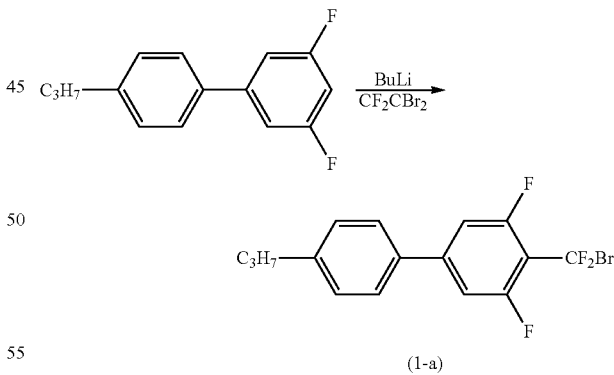

23.2 g (0.1 mol) of 3,5-difluoro-4'-propylbiphenyl and 100 mL of tetrahydrofuran are added to a 500 mL three-necked flask, the air therein is replaced with nitrogen, the temperature is decreased to $-70°$ C., 0.11 mol of BuLi is dropwise added, after finishing the addition, 10 mL of a tetrahydrofuran (THF) solution, in which 0.12 mol of $CF_2Br_2$ is dissolved, is dropwise added, the temperature is naturally increased to $0°$ C. for hydrolysis, and a conventional treatment is performed. 32 g of (1-a) having a purity of 70% is obtained.

step 2

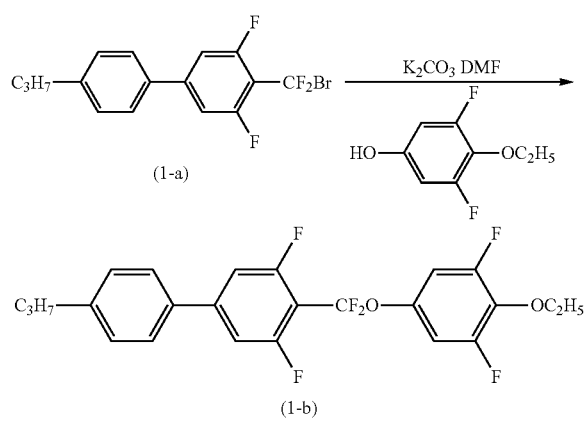

25 g (70%, 0.05 mol) of 4-(bromo-difluoro-methyl)-3,5-difluoro-4'-propyl-1,1'-biphenyl (1-a), 8.7 g (0.05 mol) of 3,5-difluoro-4-ethoxyphenol, 20 g (0.15 mol) of potassium carbonate and 300 mL of dimethylformamide (DMF) are added to a 500 mL three-necked flask, and heated to 100° C., with the temperature being maintained for 3 h. The heating is stopped to decrease the temperature to normal temperature. The material liquid is poured into 300 mL water, stirred for 5 min, and allowed to stand for liquid separation, the water phase is extracted twice with ethyl acetate, and the organic phase is washed with water to neutrality. The solvent is subjected to spin drying. Ethanol is subjected to recrystallization three times, with GC: 99.8% and yield: 45%.

Melting point (MP): 37.6° C.

In the present specification, the percentages are mass percentages, the temperatures are in degree Celsius (° C.), and the specific meanings of other symbols and the test conditions are as follows:

Cp represents the clearing point (° C.) of the liquid crystal measured by a differential scanning calorimetry (DSC) quantitative method;

S—N represents the melting point (° C.) of the liquid crystal from a crystal state to a nematic phase;

An represents the optical anisotropy, $n_o$ is the refractive index of an ordinary light, $n_e$ is the refractive index of an extraordinary light, the test condition is 25±2° C. and 589 nm, and an abbe refractometer is used for the test;

Δ∈ represents the dielectric anisotropy, Δ∈=∈$_{//}$-∈⊥, wherein ∈$_{//}$ is a dielectric constant parallel to a molecular axis, and ∈⊥ is a dielectric constant perpendicular to the molecular axis, the test condition is 25±0.5° C., a 20 micron parallel cell is used, and INSTEC: ALCT-IR1 is used for the test;

γ$_1$ represents a rotary viscosity (mPa·s), the test condition is 25±0.5° C., a 20 micron parallel cell is used, and INSTEC: ALCT-IR1 is used for the test; and ρ represents an electrical resistivity (Ω·cm), the test condition is 25±2° C., and the test instruments are a TOYO SR6517 high resistance instrument and an LE-21 liquid electrode.

VHR represents a voltage holding rate (%), and the test condition is 20±2° C., a voltage of ±5 V, a pulse width of 9 ms, and a voltage holding time of 16.7 ms. The test equipment is a TOYO Model 6254 liquid crystal performance comprehensive tester.

τ represents a response time (ms), the test instrument is DMS-501, the test condition is 25±0.5° C., the test cell is a 3.3 micron IPS test cell, both the electrode spacing and the electrode width are 9 microns, and the included angle between the frictional direction and the electrode is 90°.

T (%) represents a transmissivity, T (%)=90%*bright state (Vop) luminance/light source luminance, the test equipment is DMS501, the test condition is 25±0.5° C., the test cell is a 3.3 micron IPS test cell, both the electrode spacing and the electrode width are 9 microns, and the included angle between the frictional direction and the electrode is 9°.

In the liquid crystal monomer structures represented by codes in the present disclosure, the code representation method for the liquid crystal ring structures, terminal groups and linking groups are shown in tables 1 and 2.

TABLE 1

Corresponding code for the ring structure

| Ring structure | Corresponding code |
|---|---|
| cyclohexane | C |
| benzene | B |
| benzene (3F) | B(3F) |
| benzene (3F,5F) | B(3F,5F) |
| benzene (2F) | B(2F) |
| benzene (2F,3F) | B(2F,3F) |
| tetrahydropyran (3O) | H[3O] |
| dioxane (3O,5O) | H[3O,5O] |

TABLE 2

| Terminal group and linking group | Corresponding code |
|---|---|
| $C_nH_{2n+1}-$ | n- |
| $C_nH_{2n+1}O-$ | nO— |
| $-OCF_3$ | $-OCF_3$ |
| $-CF_2O-$ | $-CF_2O-$ |
| $-F$ | $-F$ |
| $-CH=CH-$ | $-V-$ |
| $-CH=CH-C_nH_{2n+1}$ | Vn- |

For example:

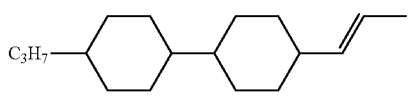

has a corresponding code of 3CCV1;

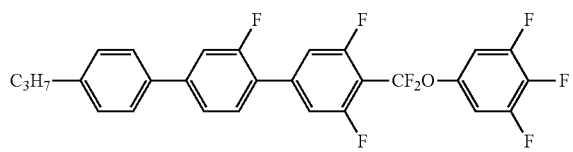

has a corresponding code of 3BB(3F)B(3F,5F)QB(3F,5F)F.

Embodiment 1

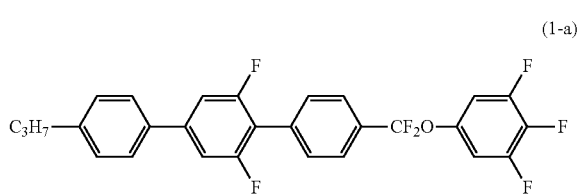
(1-a)

Synthesis Process:

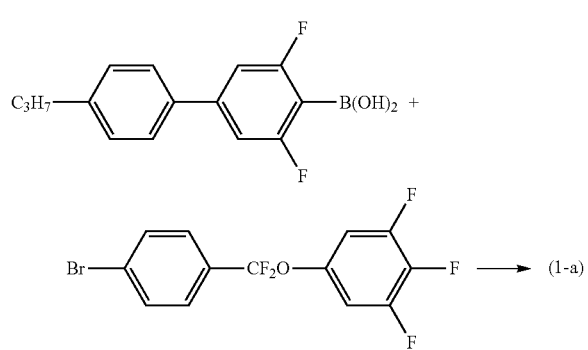

3.9 g (0.014 mol) of boric acid and 5.0 g (0.014 mol) of a bromide are fed together into a 250 mL three-necked flask, 2.5 g of potassium carbonate, 100 mL of toluene, 30 mL of water and 0.1 g of a catalyst Pd-132 are further fed therein, the air is replaced with nitrogen, and heating reflux under stirring is performed for 2 hours.

The organic phase is separated, washed with water twice, concentrated, dissolved in petroleum ether and passed through a silica gel column, and recrystallized with petroleum ether several times to obtain 3.0 g of a product with a GC purity of 99.91.

MP: 123° C.

MS: see FIG. 1.

It can be seen from the above that the structure of the product is correct.

The testing results of the liquid crystal performance of the compound are as follows:

Δn [589 nm, 20° C.]: 0.205

Δ∈ [1 KHz, 20° C.]: 25, and

Cp: 147° C.

According to the same synthesis conditions as those in this embodiment,

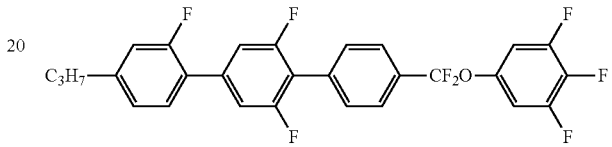

can be synthesized and obtained.

Embodiment 2

According to the same steps as those in embodiment 1, with only the reactants being correspondingly replaced according to the substituents in the product, the following compound belonging to formula I is obtained:

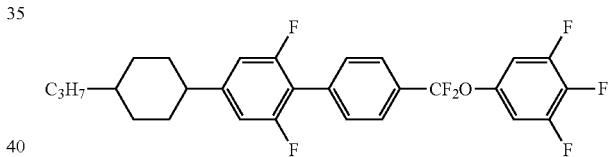

The testing results of the liquid crystal performance of the compound are as follows:

Δn [589 nm, 20° C.]: 0.163;

Δ∈ [1 KHz, 20° C.]: 25; and

Cp: 155° C.

Embodiment 3

According to the same steps as those in embodiment 1, with only the reactants being correspondingly replaced according to the substituents in the product, the following compound belonging to formula I is obtained:

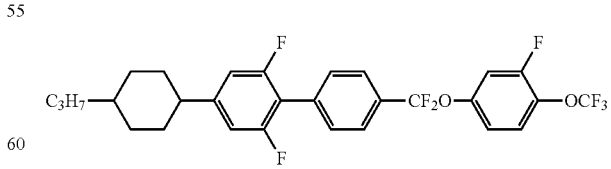

The testing results of the liquid crystal performance of the compound are as follows:

Δn [589 nm, 20° C.]: 0.148;

Δ∈ [1 KHz, 20° C.]: 30; and

Cp: 179° C.

Embodiment 4

According to the same steps as those in embodiment 1, with only the reactants being correspondingly replaced according to the substituents in the product, the following compound belonging to formula I is obtained:

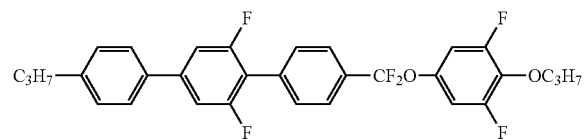

The testing results of the liquid crystal performance of the compound are as follows:

Δn [589 nm, 20° C.]: 0.228;
Δ∈ [1 KHz, 20° C.]: 15; and
Cp: 155° C.

Embodiment 5 Liquid Crystal Mixture a

The components shown in table 1 are mixed uniformly to obtain a liquid crystal mixture a provided by the present disclosure.

TABLE 1

Composition of liquid crystal mixture a

| Category | Liquid crystal monomer code | Mass percent content (%) |
|---|---|---|
| III | 3CCB(3F,4F) | 10 |
| III | 4CCBOCF3 | 10 |
| III | VCCB(3F,4F) | 12 |
| III | 2CCBB(3F,4F) | 8 |
| II | 3CCV | 18 |
| I | 3BB(3F,5F)BCF2OB(3F,4F,5F) | 6 |
| IV | 3CCB1 | 11 |
| VI | 3BB(3F,5F)CF2OB(3F,5F)O2 | 12 |
| VI | 3BB(3F,5F)CF2OB(3F,5F)4 | 13 |

The testing results of the liquid crystal performance of the liquid crystal mixture a are as follows:

Δ∈ [1 KHz, 20° C.]: 6.5;
Δn [589 nm, 20° C.]: 0.11;
Cp: 99° C.; and
$\gamma_1$: 70 mPa·s.

Embodiment 6 Liquid Crystal Mixture b

The components shown in table 2 are mixed uniformly to obtain a liquid crystal mixture b provided by the present disclosure.

TABLE 2

Composition of liquid crystal mixture b

| Category | Liquid crystal monomer code | Mass percent content (%) |
|---|---|---|
| III | 4CCB(3F,4F) | 9 |
| III | 2CCBOCF3 | 8 |
| III | VCCB(3F,4F) | 11 |
| II | 3CCV | 20 |
| II | 3CBO1 | 5 |

TABLE 2-continued

Composition of liquid crystal mixture b

| Category | Liquid crystal monomer code | Mass percent content (%) |
|---|---|---|
| I | 3BB(3F,5F)BCF2OB(3F,4F,5F) | 5 |
| I | 3CB(3F,5F)BCF2OB(3F,4F,5F) | 7 |
| IV | 3CCB1 | 6 |
| IV | VCCB1 | 11 |
| IV | VCBB2 | 6 |
| VI | 5BB(3F,5F)CF2OB(3F,5F)4 | 12 |

The testing results of the liquid crystal performance of the liquid crystal mixture b are as follows:

Δ∈ [1 KHz, 20° C.]: 6.0;
Δn [589 nm, 20° C.]: 0.10;
Cp: 96° C.; and
$\gamma_1$: 68 mPa·s.

Embodiment 7

The components shown in table 3 are mixed uniformly to obtain a liquid crystal mixture c provided by the present disclosure.

TABLE 3

Composition of liquid crystal mixture c

| Category | Liquid crystal monomer code | Mass percent content (%) |
|---|---|---|
| III | 4CCB(3F,4F) | 7 |
| III | 2CCBOCF3 | 7 |
| III | 3B(3F)BB(4F) | 6 |
| II | 3CCV | 30 |
| II | 3CCV1 | 3 |
| I | 3BB(3F,5F)BCF2OB(3F,4F,5F) | 9 |
| I | 3CB(3F,5F)BCF2OB(3F)OCF3 | 9 |
| IV | 3CCB1 | 6 |
| IV | V2CCB1 | 9 |
| VI | 5BB(3F,5F)CF2OB(3F,5F)4 | 14 |

The testing results of the liquid crystal performance of the liquid crystal mixture c are as follows:

Δ∈ [1 KHz, 20° C.]: 7.3;
Δn [589 nm, 20° C.]: 0.12;
Cp: 87° C.; and
$\gamma_1$: 67 mPa·s.

Embodiment 8

The components shown in table 4 are mixed uniformly to obtain a liquid crystal mixture d provided by the present disclosure.

TABLE 4

Composition of liquid crystal mixture d

| Category | Liquid crystal monomer code | Mass percent content (%) |
|---|---|---|
| III | 2CCB(3F,4F) | 8 |
| II | 3CCV | 35 |
| II | 3CBO1 | 2 |
| II | 1BB5 | 5 |
| I | 3BB(3F,5F)BCF2OB(3F,4F,5F) | 8 |
| I | 4CB(3F,5F)BCF2OB(3F,4F,5F) | 7 |
| I | 3B(3F)B(3F,5F)BCF2OB(3F,5F)O2 | 8 |
| IV | 3CBB1 | 8 |

TABLE 4-continued

Composition of liquid crystal mixture d

| Category | Liquid crystal monomer code | Mass percent content (%) |
|---|---|---|
| VI | 5BB(3F,5F)CF2OB(3F,5F)4 | 10 |
| VI | 5BB(3F,5F)CF2OB(3F,5F)2V | 9 |

The testing results of the liquid crystal performance of the liquid crystal mixture d are as follows:
Δ∈ [1 KHz, 20° C.]: 9.0;
Δn [589 nm, 20° C.]: 0.12;
Cp: 65° C.; and
$\gamma_1$: 66 mPa·s.

Embodiment 9

The components shown in table 5 are mixed uniformly to obtain a liquid crystal mixture e provided by the present disclosure.

TABLE 5

Composition of liquid crystal mixture e

| Category | Liquid crystal monomer code | Mass percent content (%) |
|---|---|---|
| III | 2CCB(3F,4F) | 8 |
| III | 3CCBB(3F,4F) | 5 |
| III | VCCBOCF3 | 12 |
| II | 1BB5 | 5 |
| II | 3CCV | 25 |
| I | 3BB(3F,5F)BCF2OB(3F,4F,5F) | 8 |
| I | 4CB(3F,5F)BCF2OB(3F,4F,5F) | 7 |
| I | 3B(3F)B(3F,5F)BCF2OB(3F,5F)O2 | 5 |
| IV | 3CBB1 | 6 |
| V | 3BB(2F,3F)O2 | 11 |
| VI | 5BB(3F,5F)CF2OB(3F,5F)2V | 8 |

The testing results of the liquid crystal performance of the liquid crystal mixture e are as follows:
Δ∈ [1 KHz, 20° C.]: 10.0;
Δn [589 nm, 20° C.]: 0.13;
Cp: 81° C.; and
$\gamma_1$: 65 mPa·s.

Embodiment 10

The components shown in table 6 are mixed uniformly to obtain a liquid crystal mixture f provided by the present disclosure.

TABLE 6

Composition of liquid crystal mixture f

| Category | Liquid crystal monomer code | Mass percent content (%) |
|---|---|---|
| III | 2CCB(3F,4F) | 8 |
| III | 3CCBB(3F,4F) | 5 |
| III | VCCBOCF3 | 12 |
| II | 4CCV | 5 |
| II | 3CCV | 30 |
| I | 3BB(3F,5F)BCF2OB(3F,4F,5F) | 10 |
| I | 4CB(3F,5F)BCF2OB(3F,4F,5F) | 5 |
| V | 3CB(2F,3F)O2 | 7 |
| VI | 5BB(3F,5F)CF2OB(3F,5F)2V | 8 |
| VI | 3BB(3F,5F)CF2OB(3F,5F)4 | 10 |

The testing results of the liquid crystal performance of the liquid crystal mixture f are as follows:
Δ∈ [1 KHz, 20° C.]: 8;
Δn [589 nm, 20° C.]: 0.1;
Cp: 75° C.; and
$\gamma_1$: 64 mPa·s.

Embodiment 11

The components shown in table 7 are mixed uniformly to obtain a liquid crystal mixture g provided by the present disclosure.

TABLE 7

Composition of liquid crystal mixture g

| Category | Liquid crystal monomer code | Mass percent content (%) |
|---|---|---|
| III | 2CCB(3F,4F) | 8 |
| III | 3CCB(3F,4F) | 5 |
| III | VCCBOCF3 | 10 |
| III | 3CCBOCF3 | 12 |
| II | 4CCV | 5 |
| II | 3CCV | 30 |
| II | 3CBO2 | 5 |
| I | 3H[3O,5O]B(3F,5F)BCF2OB(3F,4F,5F) | 9 |
| I | 3B(3F)B(3F,5F)BCF2OB(3F,4F,5F) | 10 |
| I | 4CB(3F,5F)BCF2OB(3F,4F,5F) | 6 |

The testing results of the liquid crystal performance of the liquid crystal mixture g are as follows:
Δ∈ [1 KHz, 20° C.]: 9.2;
Δn [589 nm, 20° C.]: 0.1;
Cp: 90° C.; and
$\gamma_1$: 66 mPa·s.

Comparative Example 1

The components shown in table 8 are mixed uniformly to obtain a liquid crystal mixture h as a control.

TABLE 8

Composition of liquid crystal mixture h

| Category | Liquid crystal monomer code | Mass percent content (%) |
|---|---|---|
| III | 2CCB(3F,4F) | 8 |
| III | 3CCB(3F,4F) | 5 |
| III | VCCBOCF3 | 10 |
| III | 3CCBOCF3 | 12 |
| II | 4CCV | 5 |
| II | 3CCV | 30 |
| II | 3CBO2 | 5 |
| | 3H[3O,5O]BB(3F,5F)CF2OB(3F,4F,5F) | 9 |
| | 3BB(3F)B(3F,5F)CF2OB(3F,4F,5F) | 10 |
| | 4CBB(3F,5F)CF2OB(3F,4F,5F) | 6 |

The testing results of the liquid crystal performance of the liquid crystal mixture h are as follows:
Δ∈ [1 KHz, 20° C.]: 9.2;
Δn [589 nm, 20° C.]: 0.11;
Cp: 92° C.; and
$\gamma_1$: 66 mPa·s.

After the liquid crystal mixture g obtained in embodiment 11 and the liquid crystal mixture g obtained in comparative example 1 are respectively filled into a liquid crystal cell, they are respectively subjected to a deterioration treatment according to the following two manners: a high-temperature treatment at 100° C. for 12 hours or a treatment under the condition of UV 5000 mJ, and the comparison of the VHR data before and after the treatments is as shown in table 9:

TABLE 9

Comparison of VHR data of liquid crystal mixtures g and h

| | Liquid crystal mixture g | | Liquid crystal mixture h | |
|---|---|---|---|---|
| | VHR (%, 5.0 V, 16.67 ms) | VHR (%, 5.0 V, 166.7 ms) | VHR (%, 5.0 V, 16.67 ms) | VHR (%, 5.0 V, 166.7 ms) |
| Before deterioration treatment | 99.65 | 99.28 | 99.65 | 99.29 |
| After high-temperature treatment | 99.59 | 99.20 | 99.49 | 99.09 |
| After UV treatment | 99.61 | 99.24 | 99.52 | 99.08 |

The deterioration data show that the liquid crystal mixture g obtained in embodiment 11 of the present disclosure has a better stability to high temperature and UV, and is more suitable for in-plane switching (IPS) and fringe-field switching (FFS) liquid crystal display.

In summary, the compounds as represented by formula I provided in the above-mentioned embodiments of the present disclosure have a large dielectric anisotropy $\Delta\epsilon$ and a moderate optical anisotropy $\Delta n$, also have a low rotary viscosity $\gamma_1$ and a good stability to high temperature and UV, have different $\Delta n$, $\Delta\epsilon$, Cp and $\gamma_1$ properties according to different $R_1$,

, $X_1$, $X_2$ and $X_3$, and thus have a wider range of application and can be used for formulating various liquid crystal mixtures with different parameters.

The invention claimed is:

1. A compound as represented by formula I,

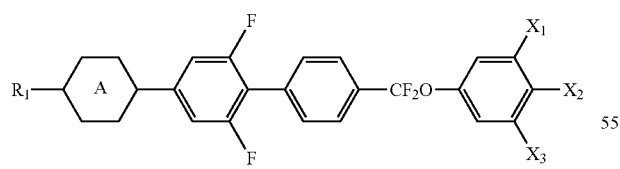

Formula I in said formula I, $R_1$ represents an alkyl having a carbon atom number of 1-9, a fluoro-substituted alkyl having a carbon atom number of 1-9, an alkoxy having a carbon atom number of 1-9, a fluoro-substituted alkoxy having a carbon atom number of 1-9, an alkenyl having a carbon atom number of 2-9, a fluoro-substituted alkenyl having a carbon atom number of 2-9, an alkenyloxy having a carbon atom number of 3-8, or an alkenyloxy having a carbon atom number of 3-8;

represents 1,4-phenylene, fluoro-substituted 1,4-phenylene, 1,4-cyclohexylidene, 1,4-cyclohexenylene, or 1,4-cyclohexylidene with one or two —CH$_2$-being substituted by oxygen atoms;

$X_1$ and $X_3$ each independently represent hydrogen or fluorine; and $X_2$ represents hydrogen, fluorine, an alkyl having a carbon atom number of 1-9, an alkoxy having a carbon atom number of 1-9, a fluoro-substituted alkyl having a carbon atom number of 1-9, a fluoro-substituted alkoxy having a carbon atom number of 1-9, or an alkenyl having a carbon atom number of 2-9;

wherein said fluoro-substituted 1,4-phenylene in said

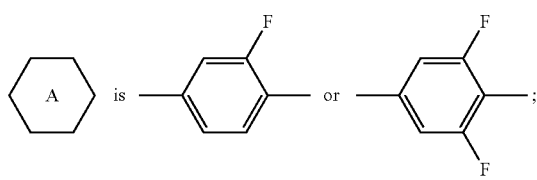

and wherein said 1,4-cyclohexylidene with one or two —CH$_2$— being substituted by oxygen atoms in said

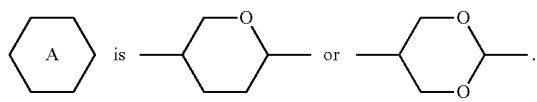

2. The compound according to claim 1, wherein said compound as represented by formula I is a compound of formula IA

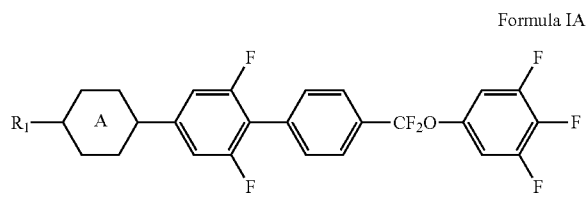

Formula IA in said formula IA, both definitions of $R_1$ and

are identical to the definitions of $R_1$ and

in claim 1.

3. The compound according to claim 2, wherein said compound as represented by formula I is any one of the compounds as represented by formulae I1 to I12:

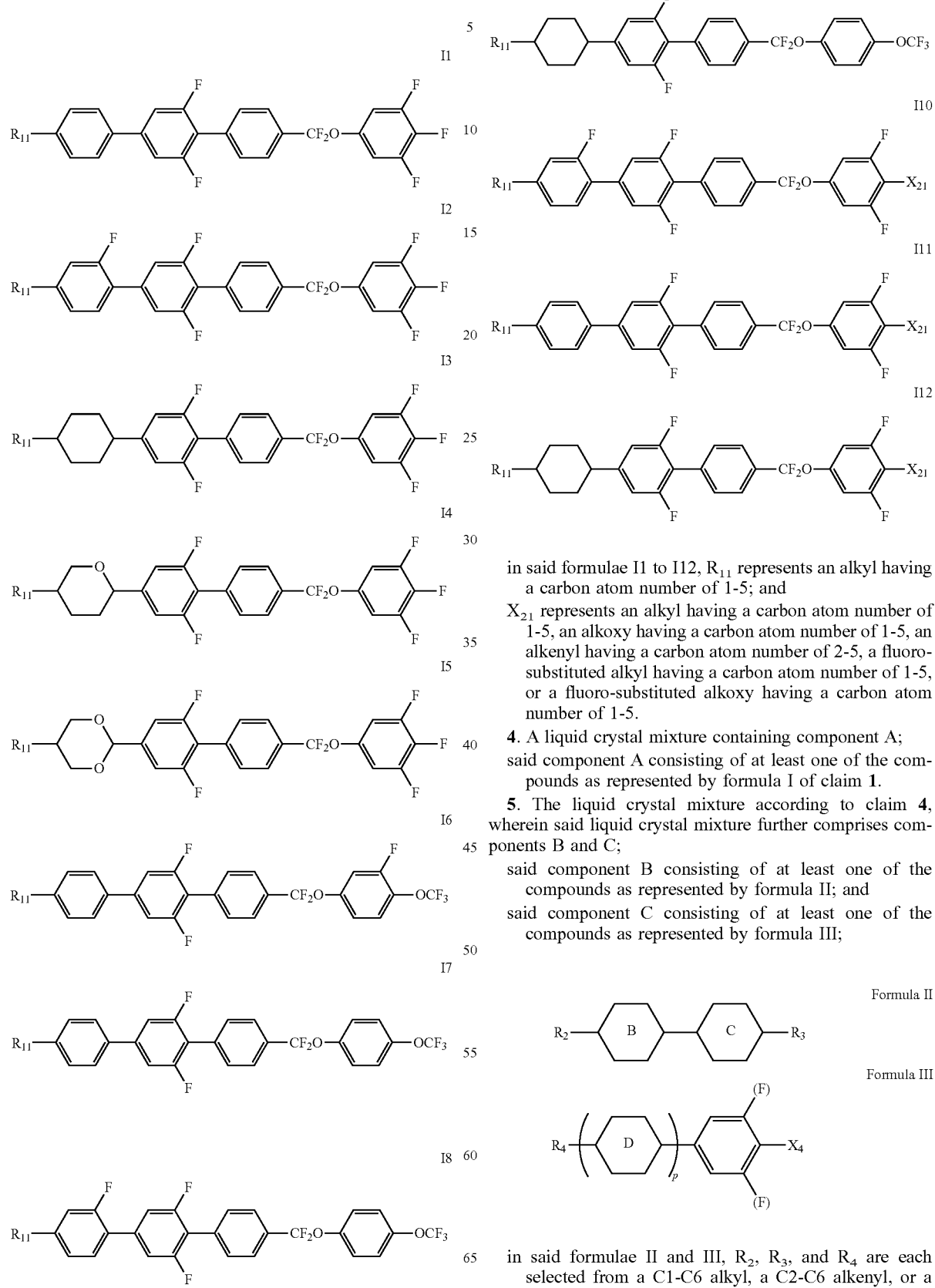

in said formulae I1 to I12, $R_{11}$ represents an alkyl having a carbon atom number of 1-5; and $X_{21}$ represents an alkyl having a carbon atom number of 1-5, an alkoxy having a carbon atom number of 1-5, an alkenyl having a carbon atom number of 2-5, a fluoro-substituted alkyl having a carbon atom number of 1-5, or a fluoro-substituted alkoxy having a carbon atom number of 1-5.

4. A liquid crystal mixture containing component A; said component A consisting of at least one of the compounds as represented by formula I of claim 1.

5. The liquid crystal mixture according to claim 4, wherein said liquid crystal mixture further comprises components B and C;

said component B consisting of at least one of the compounds as represented by formula II; and said component C consisting of at least one of the compounds as represented by formula III;

in said formulae II and III, $R_2$, $R_3$, and $R_4$ are each selected from a C1-C6 alkyl, a C2-C6 alkenyl, or a C1-C6 alkoxy;

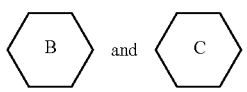

each independently represent 1,4-cyclohexylidene, 1,4-cyclohexenylene, or 1,4-phenylene;

is selected from at least one of 1,4-cyclohexylidene, 1,4-cyclohexenylene, 1,4-phenylene, and fluoro-substituted 1,4-phenylene;

p is 2 or 3;

(F) represents H or F;

$X_4$ is F, Cl, or —$OCF_3$; and wherein said fluoro-substituted 1,4-phenylene in said

represents

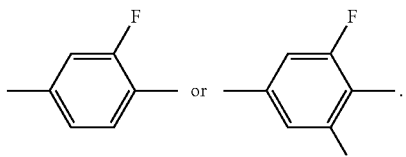

6. The liquid crystal mixture according to claim 5, wherein said liquid crystal mixture consists of components A, B, and C.

7. The liquid crystal mixture according to claim 5, wherein said compound as represented by formula II is any one of the compounds as represented by formulae II1 to II13:

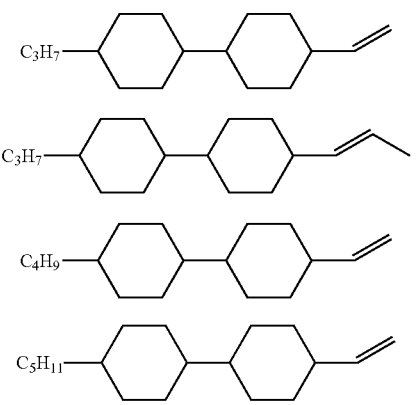

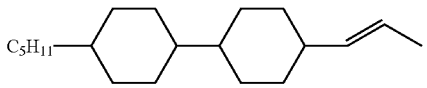

II5

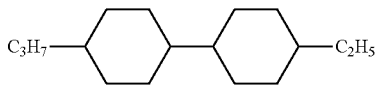

II6

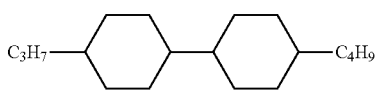

II7

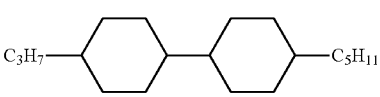

II8

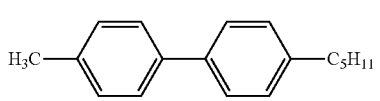

II9

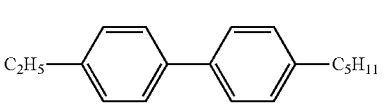

II10

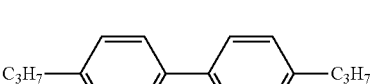

II11

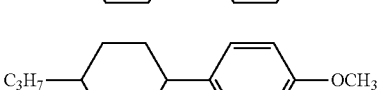

II12

II13 said compound as represented by formula III is any one of the compounds as represented by formulae III1 to III22:

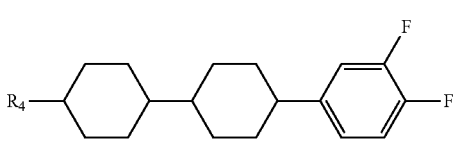

III1

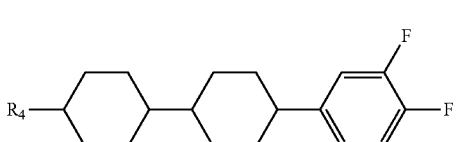

III2

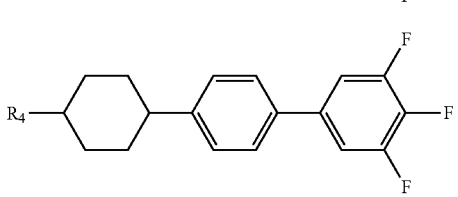

III3

-continued
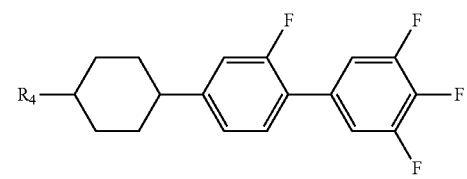 III4
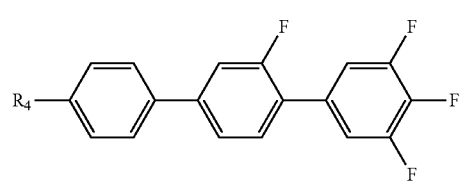 III5
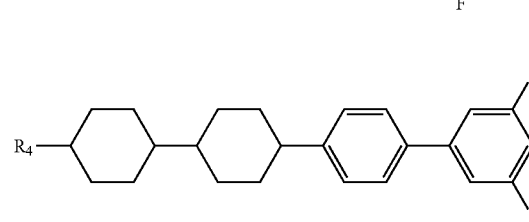 III6
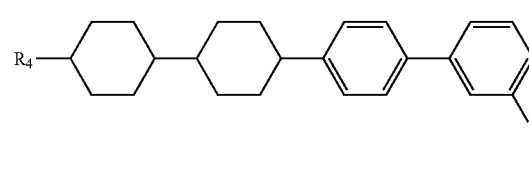 III7
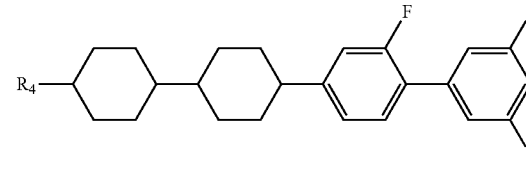 III8
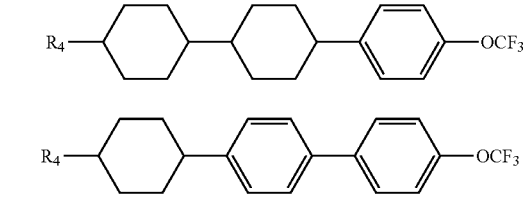 III9
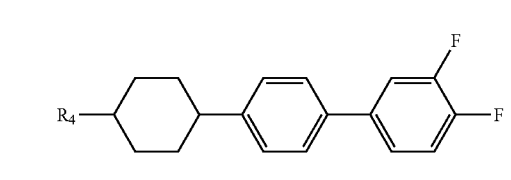 III10
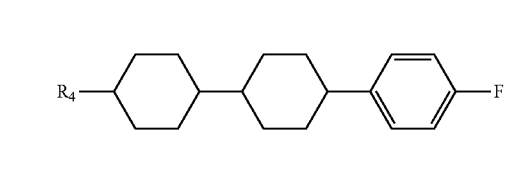 III11
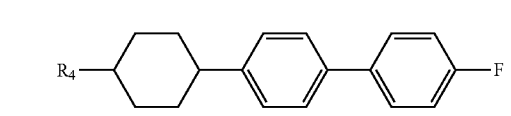 III12
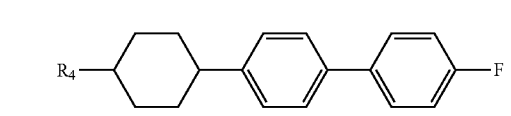 III13
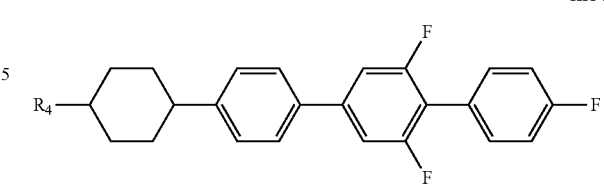 III14
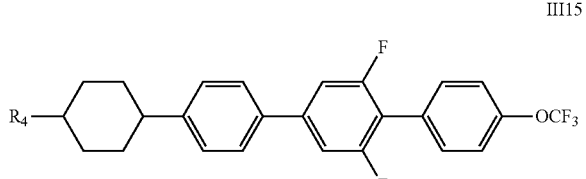 III15
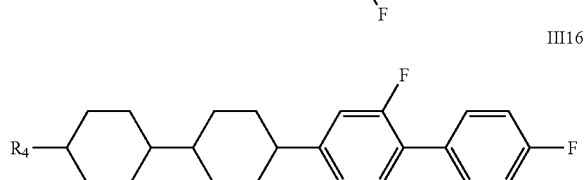 III16
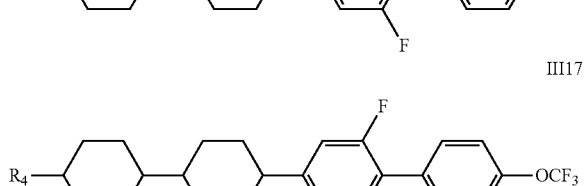 III17
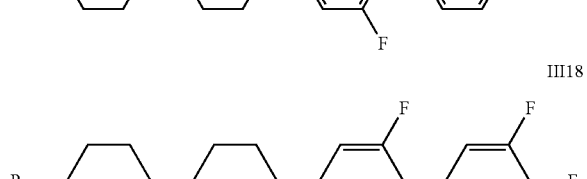 III18
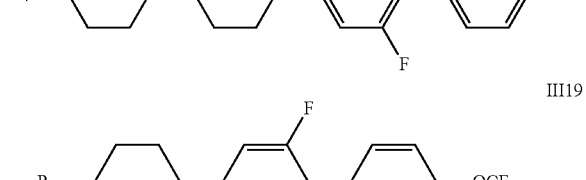 III19
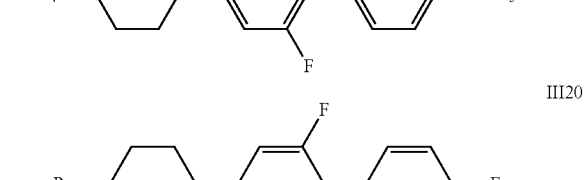 III20
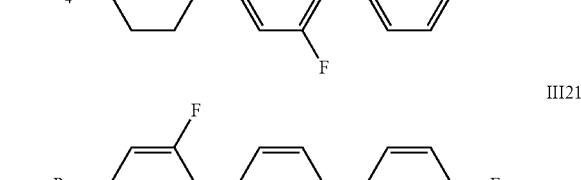 III21
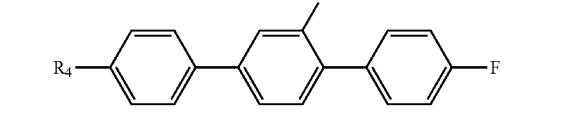 III22 in said formulae III1 to III22, $R_4$ is selected from at least one of a C1-C6 alkyl, a C2-C6 alkenyl, and a C1-C6 alkoxy.

8. The liquid crystal mixture according to claim 5, wherein said liquid crystal mixture further comprises at least one of components D, E and F;

said component D consists of at least one of the compounds as represented by formula IV;

Formula IV

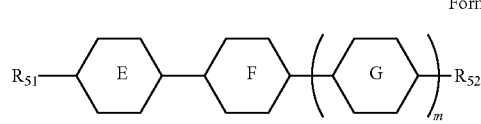

in said formula IV, $R_{51}$ and $R_{52}$ are each selected from any one of a C1-C6 alkyl, a C2-C6 alkenyl, and a C1-C6 alkoxy;

m is 1 or 2; and

are each selected from at least one of 1,4-cyclohexylidene, 1,4-cyclohexenylene, 1,4-phenylene, and fluoro-substituted 1,4-phenylene;

said component E consists of at least one of the compounds as represented by formula V;

Formula V

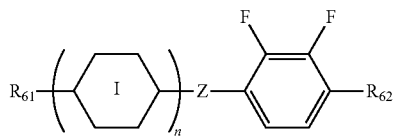

in said formula V, $R_{61}$ and $R_{62}$ are each selected from any one of a C1-C6 alkyl, a C2-C6 alkenyl, and a C1-C6 alkoxy;

n is 1 or 2;

is selected from at least one of 1,4-cyclohexylidene, 1,4-cyclohexenylene, 1,4-phenylene, and fluoro-substituted 1,4-phenylene;

Z is a single bond, —$CH_2O$—, —COO—, or —$CH_2CH_2$—; and said component F consists of at least one of the compounds as represented by formula VI;

Formula VI

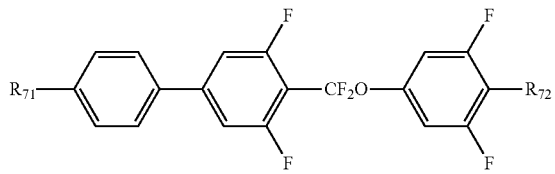

in said formula VI, $R_{71}$ and $R_{72}$ are each selected from any one of a C1-C6 alkyl, a C2-C6 alkenyl, and a C1-C6 alkoxy; and wherein said fluoro-substituted 1,4-phenylene in said

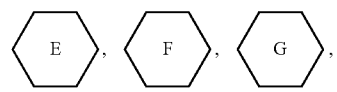

and

represents

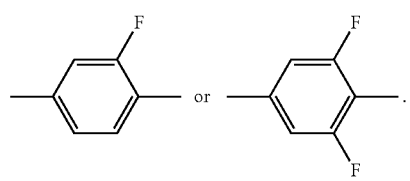

9. The liquid crystal mixture according to claim 8, wherein mass parts of the components in said liquid crystal mixture are as follows, respectively:

component A: 5-25 parts;
component B: 15-45 parts;
component C: 5-45 parts;
component D: 5-25 parts;
component E: 5-25 parts; and
component F: 5-25 parts.

10. A liquid crystal display element or liquid crystal display containing the compound as represented by formula I of claim 1; and said liquid crystal display element or liquid crystal display is an active matrix-addressing liquid crystal display element or an active matrix-addressing liquid crystal display;

wherein said active matrix-addressing liquid crystal display element is a TN-TFT, IPS-TFT, or FFS-TFT liquid crystal display element; and wherein said active matrix-addressing liquid crystal display is a TN-TFT, IPS-TFT, or FFS-TFT liquid crystal display.

* * * * *